United States Patent [19]

Jackson et al.

[11] Patent Number: 5,716,355
[45] Date of Patent: Feb. 10, 1998

[54] TRANSVERSE CONNECTION FOR SPINAL RODS

[75] Inventors: Roger P. Jackson, Prairie Village, Kans.; Paul J. Wisnewski, Cordova, Tenn.

[73] Assignee: Sofamor Danek Group, Inc., Memphis, Tenn.

[21] Appl. No.: 419,100

[22] Filed: Apr. 10, 1995

[51] Int. Cl.$^6$ .................................................. A61B 17/56
[52] U.S. Cl. ................................................ 606/61; 606/60
[58] Field of Search ............................... 606/61, 72, 73, 606/60, 53; 623/17

[56] References Cited

U.S. PATENT DOCUMENTS

| | | |
|---|---|---|
| 4,361,141 | 11/1982 | Tanner . |
| 4,433,677 | 2/1984 | Ulrich et al. . |
| 5,005,562 | 4/1991 | Cotrel . |
| 5,167,661 | 12/1992 | Wagenknecht . |
| 5,181,917 | 1/1993 | Rogozinski . |
| 5,196,013 | 3/1993 | Harms et al. . |
| 5,261,907 | 11/1993 | Vignaud et al. . |
| 5,275,600 | 1/1994 | Allard et al. . |
| 5,352,224 | 10/1994 | Westermann . |

*Primary Examiner*—Michael Powell Buiz
*Assistant Examiner*—David O. Reip
*Attorney, Agent, or Firm*—Woodard, Emhardt, Naughton Moriarty & McNett

[57] ABSTRACT

Four versions of clamps originally slidable along two generally parallel spinal rods are swivel connected to three versions of transverse connectors located between the rods. Set screws lock the transverse connectors to the clamps. Two of the clamp versions use interfitting rotational index locking detents at the swivel connections to fix the final orientation of the transverse connector relative to the spinal rods. The other two clamp versions use locking tapers to lock the rotational index positions at the swivel connections to fix the final orientation of the transverse connector relative to the spinal rods. One clamp version uses a separate set screw to fix the clamp on the spinal rod. One transverse connector has an open clamping head for installation directly onto the spinal rod without sliding it onto the rod from one end or the other.

19 Claims, 5 Drawing Sheets

TRANSVERSE CONNECTION FOR SPINAL RODS

BACKGROUND OF THE INVENTION

1. Field of the Invention

This invention relates generally to spinal osteosynthesis, and more particularly to a system for making connections between two spinal rods.

2. Description of the Prior Art

In spinal osteosynthesis, there are many cases in which implanted apparatus include laterally spaced implanted rods. Usually the positioning of the rods relative to each other must be stabilized, and various devices are used for that purpose. In U.S. Pat. No. 5,005,562 issued Apr. 9, 1991 to Yves Cotrel, transverse threaded rods 22 have hooks 23 screwed onto them. The hooks are fixed to the spinal rods 3 by hexagonal headed set screws or bolts. In U.S. Pat. No. 5,261,907 issued Nov. 16, 1993 to Vignaud et al., the pedicular screw 3 is anchored in bone and is attached to ring 9 by screwing down screw 6 which simultaneously spreads the screw head 5 to lock on ring 9, and also clamps the rod 2. Transverse rods 10, fixed in the rings 9, are received in clamping collar 11 and, when oriented in desired position, are fixed in collar 11 by the common clamping screw 12. There has remained a need for a device enabling rigid connection between two rods and which accommodates some variation in initial relative positioning of the rods, does not require mounting directly to screws such as in Vignaud et al., enables passage between vertebrae, and has minimal bulk. The present invention is addressed to that need.

SUMMARY OF THE INVENTION

Described briefly, according to a typical embodiment of the present invention, clamps originally slidable along two generally parallel spinal rods are swivel connected to a transverse connector located between the rods. Set screws lock the transverse connector to the clamps. One embodiment of clamp uses a separate set screw to fix the clamp on the spinal rod. The clamps use interfitting rotational index locking detents at the swivel connections to fix the final orientation of the transverse connector relative to the spinal rods. Other embodiments use locking tapers to lock the rotational index positions at the swivel connections to fix the final orientation of the transverse connector relative to the spinal rods.

DESCRIPTION OF THE PREFERRED EMBODIMENT

Figure 1:
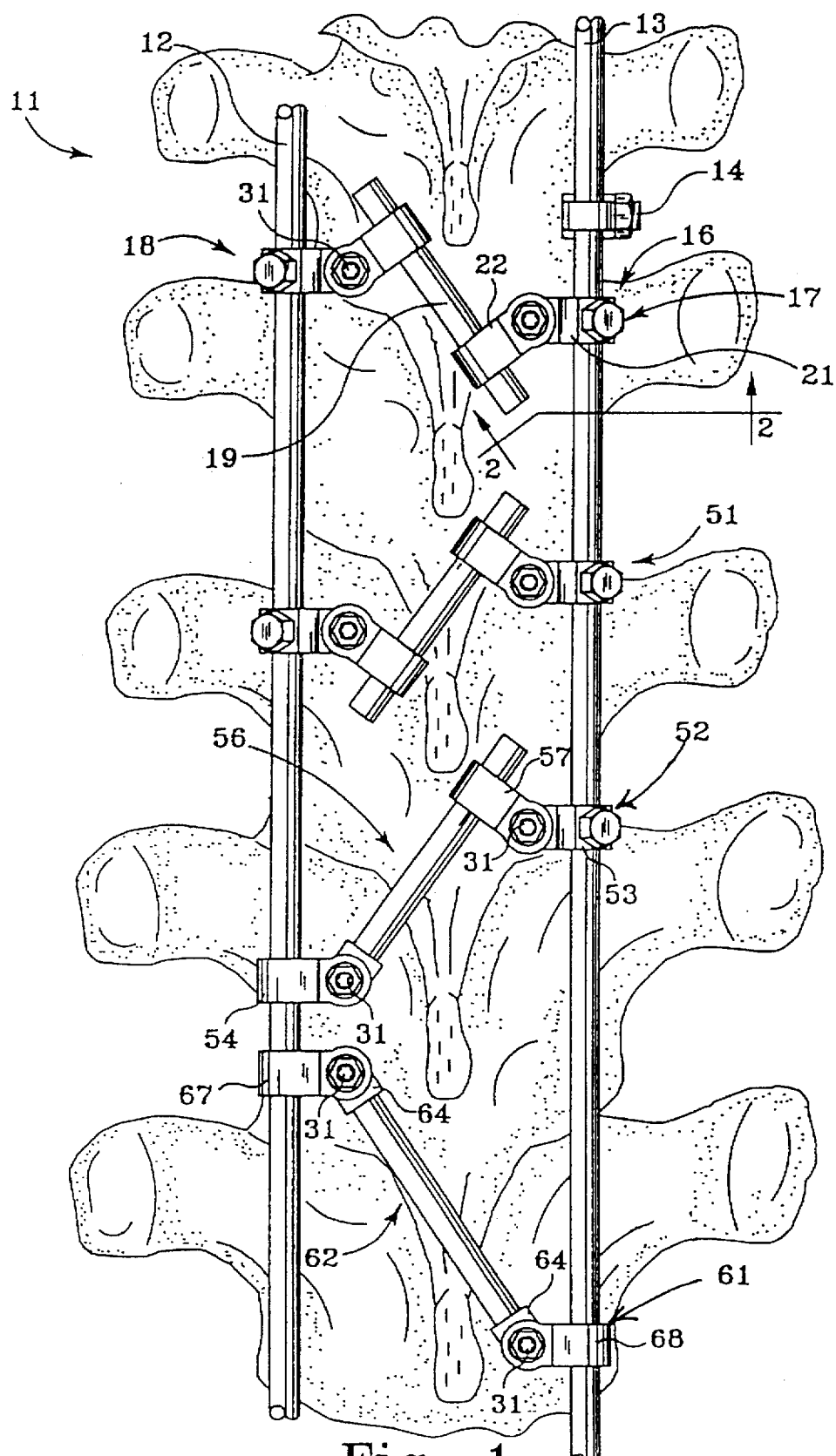
FIG. 1 is a fragmentary posterior view of a spinal column with a corrective implant system incorporating transverse connection devices according to various embodiments of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings in detail, in FIG. 1 there is the spinal column shown generally at 11 with two spinal rods 12 and 13 thereon and, for purposes of illustration, one hook assembly 14 securing the rod 13 to one of the bones. It should be understood that the rods can be secured in several additional places to the spinal column by appropriate hooks such as are well known in the art, some examples of which are shown in the above-mentioned Cotrel patent and others in the TSRH Spinal Implant System described in the "Surgical Technical Manual" of Danek Medical, Inc. published in 1990, the disclosure of which is incorporated herein by reference. That particular literature describes CROSSLINK devices to provide fixed spacing between rods 12 and 13.

Figure 2:
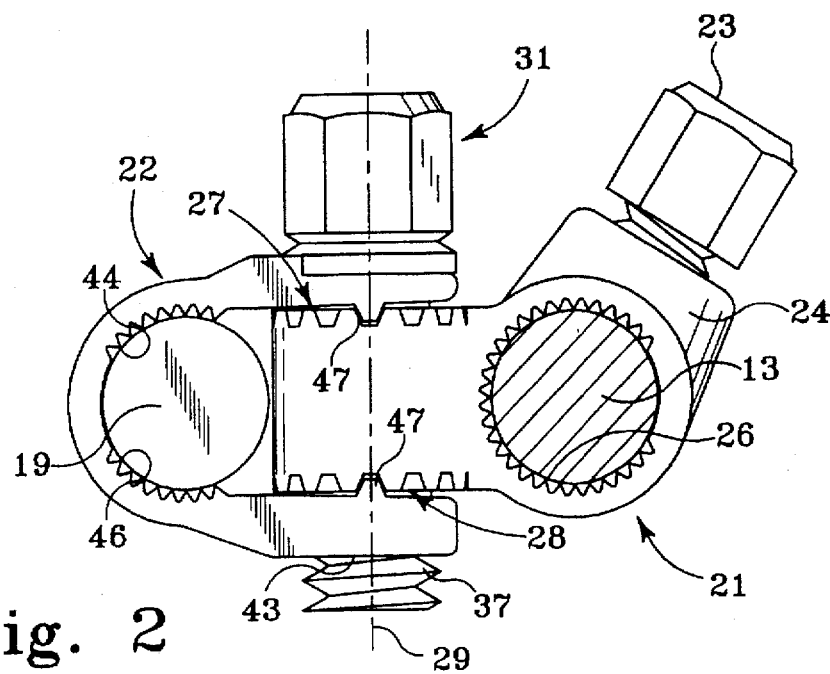
FIG. 2 is a view taken at line 2—2 in FIG. 1 and viewed in the direction of the arrows.

Several different embodiments of the present invention are illustrated in FIG. 1 herein, and another embodiment is shown in FIG. 2. Conditions to be treated in different cases may indicate the desirability of using only one embodiment or other combinations of various embodiments of the present invention.

Figure 3:
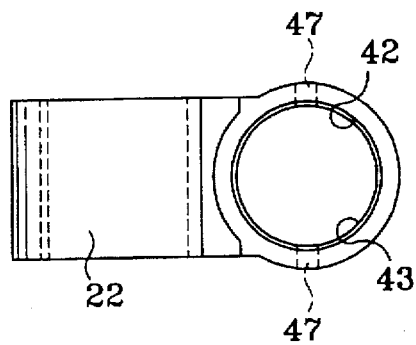
FIG. 3 is a view of a portion of one of the pivot assemblies.

The first embodiment to be described will be the transverse connector assembly 16 which includes two pivot assemblies 17 and 18 which are identical although differently oriented, and a transverse connector rod 19. The pivot assembly 17, which will be described as exemplary, includes the connector pivot base 21 and the U-clamp 22. The components are better shown in FIGS. 2 and 3. The pivot base 21 includes the aperture through which the spinal rod 13 extends. The set screw 23 is threaded into the boss 24 of the pivot base 21. There are axially extending serrations or teeth 26 in the spinal rod receiving aperture in the pivot base to assist in securing the pivot base on the rod when the screw 23 is tightened onto the rod.

The other portion of the pivot base has an aperture through it receiving a set screw 31 which serves first as a pivot pin, and then as a clamping screw. On the upper and lower faces 27 and 28, respectively, there are grooves extending radially from the axis 29 of the pin receiving aperture, thus providing a rotary indexing detent system.

Figure 10:
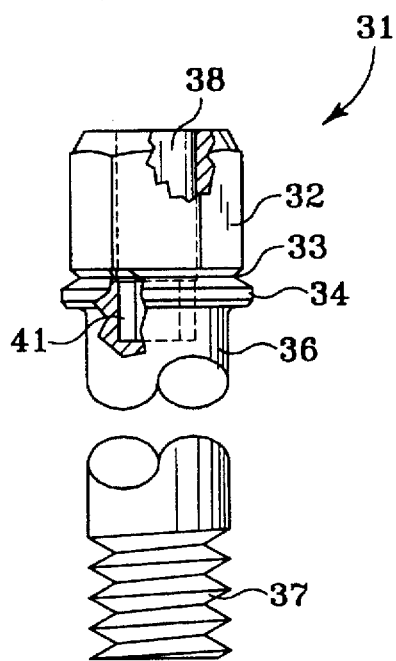
FIG. 10 is a much enlarged view of a break-off set screw used in the system.

The other portion of the pivot assembly 17 is the U-clamp 22. This clamp is secured to the transverse connector rod 19 and to the pivot base by set screw 31 which, as shown in FIG. 10, has a hexagonal head 32, a peripheral notch 33 immediately below the head, a flange 34, a smooth shank 36 and threaded distal lower end 37. The notch provides a break-off feature to prevent excessive tightening. A circular aperture 38 through the head provides access to a number 10 TORX socket 41 in the top of that portion of the set screw immediately below the notch 33. In the assembly, the threaded portion is passed freely through the aperture 42 in the top of the U-clamp (FIG. 3) and threaded into the threaded portion 43 in the bottom of the U-clamp to thereby assemble the U-clamp to the pivot base. The U-clamp has two sets of axially extending teeth 44 and 46, similar to the teeth in the spinal rod receiving bore of the pivot base. These U-clamp teeth 44 and 46 grip transverse connector rod 19 when the clamp is tightened.

Once the orientation of the clamp on the pivot base has been established and deemed acceptable by the surgeon, it is essential that the orientation remain constant. For that purpose, there are four ribs 47 on the U-clamp. Two of these, spaced diametrically apart, face downward from the top of the clamp, and two of them face upward from the bottom of the clamp. These ribs or ridges seat in the grooves in the upper and lower faces 27 and 28, respectively, of the pivot base. The grooves are in a sunburst array around the axis 29 of the pin receiving aperture in the pivot base. The ability to interfit the ridges 47 of U-clamp 22 in the grooves in the top and bottom surfaces of the pivot base enables locking these two parts in any of many possible rotational index positions chosen by the surgeon.

The pivot assembly 18 on the spinal rod 12 is exactly the same as assembly 17 just described on spinal rod 13. The orientation is different as shown in FIG. 1, with the transverse connector rod 19 spanning the gap between the two U-clamps on the respective pivot assemblies. It is a feature of this invention that there is great freedom of discretion in the location and orientation of the pivot assemblies and the transverse connector. The assembly allows for the necessary degrees of tilt, rotation and angulation in three planes to make connections possible regardless of what the anatomy instrumented or deformity treated might be. It allows for dynamic diagonal transverse connections with both distraction and compression force applications. The sequence of tightening the set screws 23 for the pivot bases to the spinal rods and screws 31 for the U-clamps to the pivot bases can be selected in accordance with the preferences of the surgeon, to provide the best possible relationship of the parts. At such time as the desired relationship of the U-clamps to the pivot bases has been determined, the set screws 31 can be tightened by a hexagonal wrench on the heads 32. They are designed to break at the notch 33 to avoid excessive application of tightening torque. If, at some later time, it is desired to remove the set screws, a suitable TORX wrench can be used in the socket 41 for that purpose.

Referring further to FIG. 1, there is a second transverse connector assembly 51 shown connected between the two rods 12 and 13. The components of this connector assembly are exactly the same as those for the assembly 16, the only difference being that the pivot base on the right-hand rod is above that on the left-hand rod.

Figure 7A:
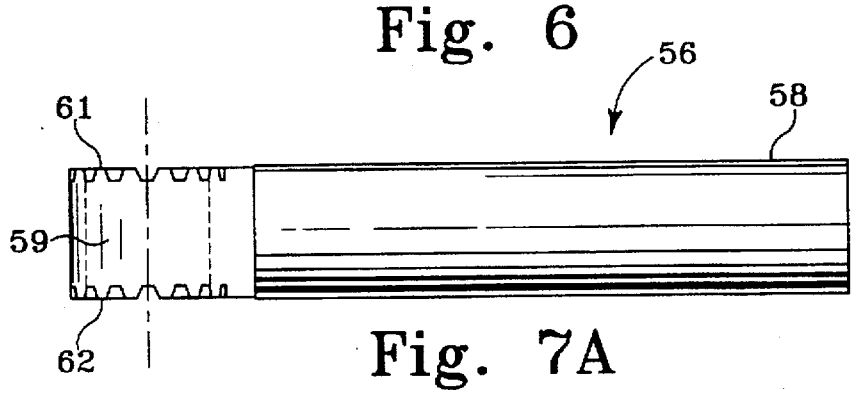
FIG. 7A is an elevational view of one connector rod embodiment.
Figure 7B:
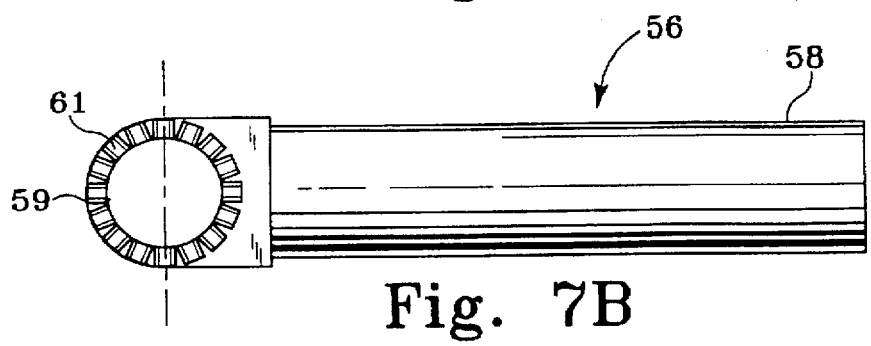
FIG. 7B is a top plan view of the FIG. 7A component.

Referring still further to FIG. 1, there is a third transverse connector assembly 52. This one is different from the first two in several respects. A pivot base and U-clamp assembly 53 is secured to the rod 13 in the same manner as described above with reference to the assembly 17. But on the other rod 12, the pivot assembly has only the U-clamp portion 54 of an assembly such as 53. The U-clamp 54 is exactly like U-clamp 22. Instead of the transverse connector rod 19 previously described, the transverse connector 56 as shown in FIG. 7A and 7B has a cylindrical rod portion 58 and, at one end of it, there is a double faced swivel head portion 59 having an upper surface 59a and lower surface 59b, both of which have the radially extending grooves in a sunburst array as was described above for the pivot base 21. These are received in the U-clamp 54 just as the comparable portion of the pivot base 21 is received in the U-clamp 22. This swivel connection is secured in the same way with the same type of set screw 31 as described above. The cylindrical portion 58 of the rod is received through the U-clamp 57 (which is exactly like U-clamps 54 and 22) and is secured in the same way as described above for the rod 19 in U-clamp 22.

Figure 8:
FIG. 8 is an elevational view of another connector rod embodiment.

Referring further to FIG. 1, a fourth transverse connector assembly 61 is shown connected between the rods 12 and 13. In this example, the transverse connector 62 is as shown in FIG. 8 and is similar to connector 56 described above, but the cylindrical rod portion 63 has swivel head portions 64 at both ends. These are like the swivel head 59 at the end of the rod 58 and are received in U-clamps 67 and 68 on rods 12 and 13, respectively. Set screws 31 are used in both of the U-clamps to clamp them to the swivel heads 64 of the rod 62 when the desired spacing and location of the rod 62 have been determined. U-clamps 67 and 68 are like U-clamp 22 and the clamping is the same as described above for fixing the U-clamp 22 to pivot 21.

Figure 4:
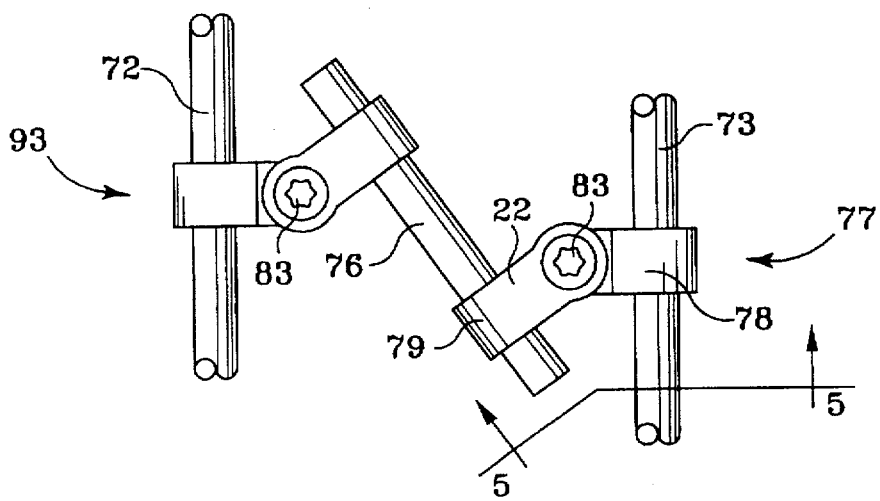
FIG. 4 is a view similar to FIG. 1 but showing a still further embodiment.

Referring now to FIG. 4, spinal rods 72 and 73 are shown. It should be understood that the spinal rods in FIGS. 1 and 2 can be closer together or farther apart, and the only resulting change would be the orientation of the connector assemblies and the transverse rod between them. Therefore, any of the three different connector assemblies in FIG. 1 can be used with a greater or lesser spacing between the spinal rods. This is true of the embodiment shown in FIG. 4. The transverse connector assembly in FIG. 4 appears very similar to and is similarly oriented to that shown at the top of FIG. 1., but there are some differences, as can be better understood by reference to FIGS. 5 and 6. In this case, the transverse rod 76 can be the same as rod 19 in FIG. 1. But the pivot assembly 77 includes two clamps 78 and 79. In a sense, both of these clamps 78 and 79 might be considered U-clamps. But to distinguish them, the clamp 78 will be referred to as a split clamp and 79 as a U-clamp. Clamp 78 has the longitudinally or axially extending alternate ridges or grooves or (teeth) 81 therein to tightly engage the spinal rod 73 when clamped shut. Similarly, clamp 79 has the axially extending alternate ridges and grooves 82 for gripping tightly on transverse rod 76 when the assembly is clamped together. For clamping the assembly together, a set screw 83 is used and is provided with a Morse taper on its exterior surface 84 received in a matching Morse taper 85 in the upper finger of clamp 79, and matching Morse taper 86 in the clamp 78. The threads 87 on the lower end of the set screw 83 are threaded into the threads 88 of the clamp 79. A Morse taper is also provided on surface 91 of the clamp 78 so that it does not matter whether the clamp is used as shown or upside down, as the set screw 83 will lock in whichever of the apertures 86 or 91 is at the top. The set screw 83 can be provided with a break off head as described above with reference to the set screw 31, or with simply a TORX or hexagonal socket 92 therein. Upon reception of the clamps 78 and 79 on rods 73 and 76, respectively, and upon suitable orientation of the rods with respect to each other and the suitable orientation of the clamps on the rods, the set screws can be tightened to clamp both of the clamps onto their respective rods, with the set screws locking in their respective tapers such as 86 in the upper finger of clamp 78 and surface 85 in the upper finger of clamp 79. The connector clamp assembly 93 on rod 72 is exactly the same as clamp assembly 77 on rod 73 and is clamped to rod 72 and rod 76 in the same way. A shallow, semi-circular channel 94, half of which is on the lower finger of clamp 78 and half on the upper finger of clamp 78, extends around the entire exposed surface of the two fingers so as to accommodate the rod 76 during the swiveling of the clamp 79 on clamp 78 before locking the two together with the set screw.

Figure 5:
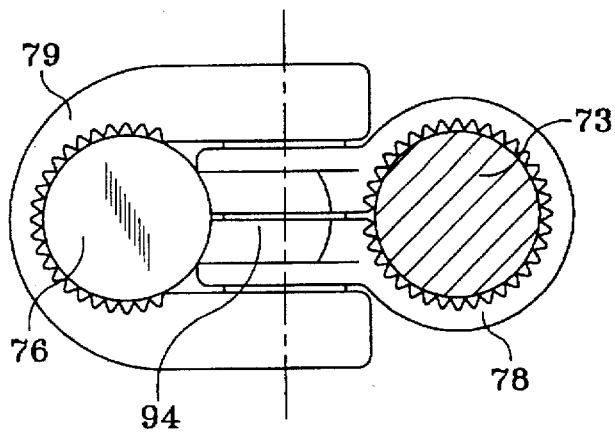
FIG. 5 is a sectional view taken at line 5—5 in FIG. 4 and viewed in the direction of the arrows.
Figure 6:
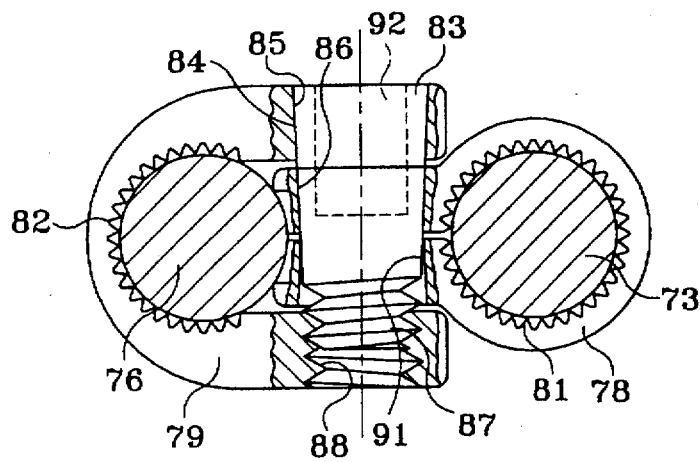
FIG. 6 is a fragmentary section of the assembly of FIG. 5.
Figure 9:
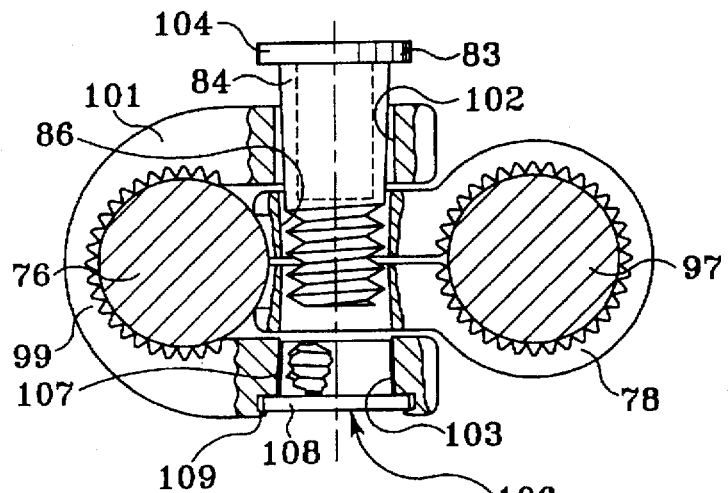
FIG. 9 is a view similar to FIG. 6 but of a still further connector assembly.

Referring now to FIG. 9, a variation of the embodiment of FIGS. 5 and 6 is shown. In this pivot assembly example, the spinal rod 97 and the transverse rod 76 are associated with two clamps, one being clamp 78 as previously described with reference to FIGS. 5 and 6, but the other being a U-clamp 99 which is different from clamp 79. One of the differences is the fact that the upper finger 101 thereof has the aperture 102 which is a straight walled cylindrical aperture and does not lock on the taper 84 of the locking screw 83. Another difference is that there is a tapered aperture with a Morse taper at 103 in the lower finger of the clamp. The locking screw 83 is the same as that in the previously described embodiment, except that in this embodiment it has an upper flange 104 to engage and bear on the upper surface of the upper finger 101. The threaded end of this screw is received in a lock nut 106 which has a tapered external surface 107, and a flange 108 on its lower end. Therefore, when this assembly is to be clamped on the rods 97 and 76, the screw 83 is turned down to engagement of the threads thereon with the threads in the bore of the nut 106 which then jams in the Morse taper in the lower finger of the clamp 99 and, upon sufficient tightening, the flange 104 on the head of screw 83 will pull the clamp 99 into clamping engagement with rod 76. The engagement of the Morse taper 84 on the screw 83 with the taper 86 in the clamp 78 will pull that clamp tightly onto rod 97 and lock the screw in the clamp. The edges 109 at the bottom of the aperture in the lower finger of clamp 99 can be bent over to trap the flange 108 of the lock nut in the assembly so that it does not fall out before the screw threads engage it.

Figure 11:
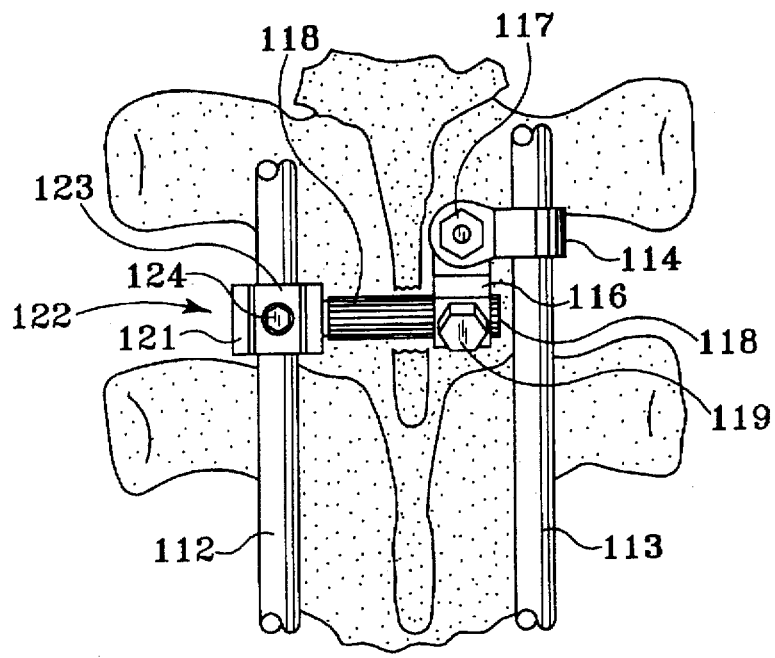
FIG. 11 is a view similar to FIGS. 1 and 4 but showing a lateral connector with an open clamp to one of the spinal rods.
Figure 12:
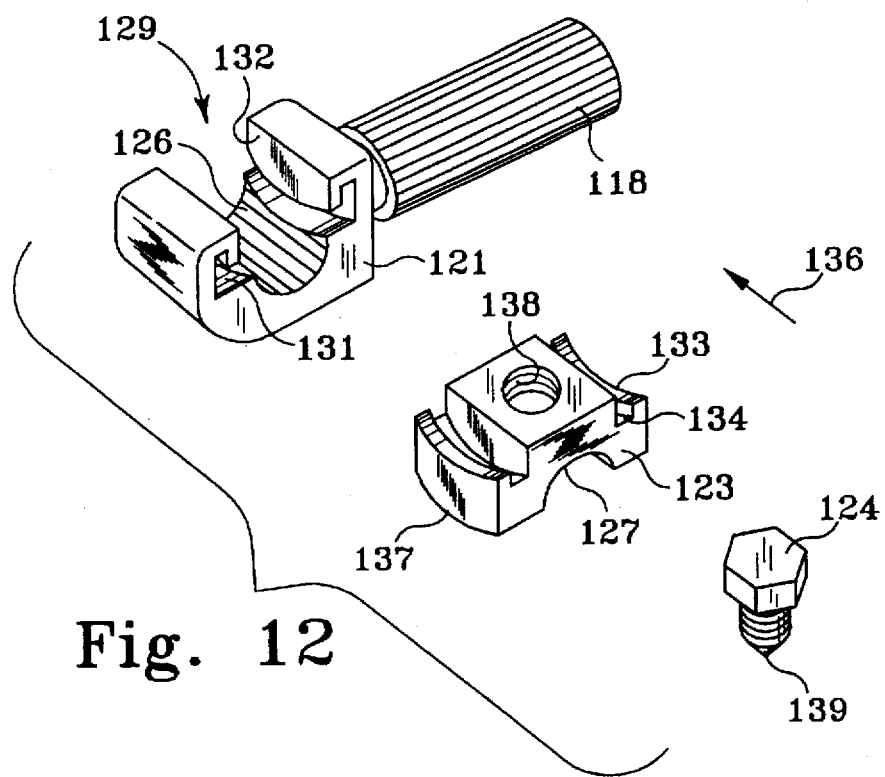
FIG. 12 is an exploded view of the lateral connector with the open clamp.

Referring now to FIGS. 11 and 12, the spinal rods 112 and 113 can be considered comparable and situated similarly to those in FIGS. 1 and 4, for example. A U-clamp 114 is secured to rod 113. This clamp can be identical to clamp 22 shown in FIGS. 1-3 but, instead of being secured to the transverse rod as in those figures, it is secured directly to the spinal rod 113. A pivot base 116 is mounted to the U-clamp 114. This pivot base is identical to pivot base 21 in FIGS. 1 and 2. It is mounted to the U-clamp 114 in exactly the same way and secured by the set screw 117, which simultaneously secures the U-clamp 114 to the spinal rod 113. In this example, in contrast to the FIG. 1 illustration, the U-clamp and the pivot base are shown at 90° with respect to each other but, as in the previous example, the angle between the parts, once established as desired, is fixed by the ribs on the U-clamp received in the grooves in the pivot base to securely maintain that angular relationship.

The transverse connector rod 118 is received and fixed in the aperture of the pivot base 116 by the set screw 119 in exactly the same manner as the spinal rod 13 is secured in pivot base 21 by set screw 23 in FIG. 2. This transverse connector rod 118 is integral with the connector base 121 of the open-type connector clamp assembly 122 which includes a connector cap 123 secured to the base and to the spinal rod 112 by the set screw 124.

Referring now to FIG. 12, the transverse connector rod-base and clamp assembly 122 is shown in three pieces, with the connector rod 118 and base 121 separate from the cap 123 and set screw 124. The rod 118 itself has a knurled surface as does the groove 126 in the base. Similarly, although not shown, the groove 127 in the cap is knurled. As may be evident from the description to this point, the base is open so that it can be installed on the spinal rod in a transverse direction without having to slide it axially down the length of the rod. In other words, the entrance gap to the spinal rod receiver channel is wide enough for the spinal rod to be received in it in the direction of arrow 129. Grooves 131 are provided at each side of the spinal rod receiver channel. The lower surface of each groove has a slight concave curve to it, and the flange 132 at the top of the base at each side of the channel entrance has a convex curve to it. Similarly, the cap 123 has a flange 133 at each side which extends parallel to the axis of the rod receiving channel 127, whereby the cap can be installed into the base in the direction of arrow 136, with the flanges on the cap received in the grooves 131 outboard of the flanges 132 on the base, the flanges 132 of the base being received in the grooves 134 in the cap. Because of the fact that the top of flange 133, bottom of flange 132 and the bottom of the groove 134 in the cap and the bottom of the groove 131 in the base are all curved, so is the bottom 137 of the cap. Therefore a slight rocking motion of the cap as it is inserted in the direction of arrow 136 into the base, will occur. Therefore, the total clearance between the cylinder formed by the rod receiving channel 127 in the cap and the rod receiving channel 126 in the base will be enough to admit the cap into the base when the base has been positioned in place under the spinal rod. Following the installation, the set screw 124 is tightened in the threads 138 in the set screw receiver aperture in the cap. Accordingly, the set screw drives the spinal rod tightly against the bottom of channel 126 in the base. The bottom of the set screw is pointed as at 139 to avoid any axial slippage along the spinal rod. Axial movement of the base along the spinal rod is limited not only by the friction between the channel bottom and the rod but also by the fact that, due to the curvature in the flanges and receiver grooves in the base and the cap, axial movement of the base cannot take place without tending to rotate it about the axis of the rod 118. This movement is resisted not only by the rod 112 itself, but also by the clamping of the transverse rod 118 in the pivot base and by the pivot base being clamped in the U-clamp 114. Therefore, once the set screws 117, 119 and 124 are secured, movement is securely resisted in all directions.

The material for all of the components may be the same. For one example, connector 56 is a solid unit of 316L ASTM F138 grade 2 cold rolled 900/1050 MPa material. It is machined to provide the rod portion 58 and head portion 59. The spinal rods and transverse rods can be smooth, shot peened, or knurled. The transverse rods such as 19 and 58 can be cut off to a desired length.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A system for spinal osteosynthesis including two generally parallel spinal rods adapted to be implanted adjacent a spinal column, and an apparatus for making a rigid connection between the rods, the apparatus comprising:

first and second U-shaped connectors slidably connectable along a respective one of the spinal rods;

a transverse connector for location between the spinal rods;

third and fourth U-shaped connectors slidably connected to said transverse connector; and two fasteners, one of the fasteners connecting the first U-shaped connector to the third U-shaped connector when said first connector is disposed on a respective spinal rod and the third connector is connected to said transverse connector, the other of the fasteners connecting the second U-shaped connector to the fourth U-shaped connector when said second connector is disposed on a respective spinal red and the fourth connector is connected to said transverse connector, wherein said two fasteners are operable to clamp said first and third U-shaped connectors together while simultaneously clamping said first and third connectors to a respective spinal rod, and to clamp said second and fourth U-shaped connectors together while simultaneously clamping said second and fourth connectors to said transverse connector for locking said transverse connector at variable orientations relative to the spinal rods.

2. The apparatus of claim 1 and further comprising:

third and fourth fasteners, the third fastener clamping the first connector to the first rod, and the fourth fastener clamping the second connector to the second rod.

3. In a system for spinal osteosynthesis including two generally parallel spinal rods implanted adjacent a spinal column, an apparatus for making a rigid connection between rods comprising:

first and second connectors slidable along the first and second rods, respectively;

a transverse connector for location between the rods and swivel connected to the first and second connectors;

two fasteners;

one of the fasteners connecting the first connector to the transverse connector, the other of the fasteners connecting the second connector to the transverse connector;

swivel orientation locks at the locations of the connection of the transverse connector to the first and second connectors for locking said connector at variable orientations; and wherein the first connector is a pivot base having upper and lower indexing detent recesses circularly spaced around a pivot aperture;

a U-clamp pivotally mounted to the pivot base and having detent projections thereon receivable in the detent recesses; and one of the fasteners being a set screw operable to drive at least one of the detent projections into one of the detent recesses to thereupon prevent the U-clamp from pivoting on the pivot about the aperture.

4. The apparatus of claim 3 and wherein:

the U-clamp has upper and lower arms, the detent recesses are grooves extending radially outward from the pivot aperture the upper arm having an aperture therein receiving the one set screw therein, and the lower arm having screw threads therein receiving threads of the one set screw, the upper arm having a lower surface with at least one of the detent projections thereon projecting downward therefrom into one of the detent recesses of the pivot base, the lower arm having an upper surface with at least one of the detent projections thereon projecting upward therefrom into one of the detent recesses of the pivot base.

5. The apparatus of claim 4 and wherein:

the U-clamp has a semicylindrical portion thereof with a cylindrical axis, and has a plurality of teeth therein extending parallel to the axis thereof and gripping a rod.

6. The apparatus of claim 5 and wherein:

the one set screw is a break-off set screw.

7. In a system for spinal osteosynthesis including two generally parallel spinal rods implanted adjacent a spinal column, an apparatus for making a rigid connection between rods comprising:

first and second connectors slidable along the first and second rods, respectively;

a transverse connector for location between the rods and swivel connected to the first and second connectors;

two fasteners;

one of the fasteners connecting the first connector to the transverse connector, the other of the fasteners connecting the second connector to the transverse connector;

swivel orientation locks at the locations of the connection of the transverse connector to the first and second connectors for locating said connector at variable orientations; and wherein the first connector is a pivot base in the form of a split clamp having upper and lower arms;

a U-clamp having a portion received on the split clamp and a portion receiving the transverse connector therein; and the fastener connecting the pivot base to the transverse connector is a set screw which has a tapered portion and a threaded portion, and at least one of the split clamp and the U-clamp has a taper matching and locking on the tapered portion of the set screw.

8. The apparatus of claim 7 and wherein:

the matching taper is in the upper arm.

9. The apparatus of claim 8 and wherein:

the U-clamp has an upper arm and a lower arm, the upper arm having an aperture therein receiving a portion of the set screw therethrough, the aperture having a tapered internal wall matching the taper of the set screw, and the lower arm having an aperture therein with threads receiving the threaded portion of the set screw whereby, upon advancing the threaded portion of the set screw in the lower arm threads, the clamps are locked to each other and the split clamp is locked on the spinal rod and the U-shaped clamp is locked on the transverse connector.

10. The apparatus of claim 8 and wherein:

the set screw has an upper flange engageable with the top of the upper arm of the split clamp;

the U-clamp has an upper arm and a lower arm and an aperture in the lower arm and which has a taper therein, the apparatus further comprising:

a nut received in the aperture in the lower arm of the U-clamp, the nut having an external taper matching the taper in the lower arm of the U-clamp, and the nut having internal threads receiving the threaded portion of the set screw whereby the set screw is securable in the nut and the nut is lockable in the taper in the lower arm of the U-clamp and the taper on the set screw is lockable in the taper in the upper arm of the split clamp to thereby lock the clamps to each other and lock the split clamp on the spinal rod and lock the U-clamp on the transverse connector.

11. In a system for spinal osteosynthesis including two generally parallel spinal rods implanted adjacent a spinal column, an apparatus for making a rigid connection between rods comprising:

first and second connectors slidable along the first and second rods, respectively;

a transverse connector for location between the rods and swivel connected to the first and second connectors;

two fasteners;

one of the fasteners connecting the first connector to the transverse connector, the other of the fasteners connecting the second connector to the transverse connector;

swivel orientation locks at the locations of the connection of the transverse connector to the first and second connectors for locking said connector at variable orientations; and wherein the first and second connectors are pivot bases and the fasteners are set screws threaded through the pivot bases and operable to fix the pivot bases on their respective rods;

first and second swivel clamps pivotally mounted to the first and second pivot bases;

the transverse connector being a rod extending through the first and second clamps; and third and fourth set screws serve as clamp set screws and connect the clamps to their respective pivot bases and lock the clamps on the pivot bases and on the transverse connector rod.

12. The apparatus of claim 11 and wherein:

the clamps and transverse connector rod are disposed between the first and second spinal rods.

13. The apparatus of claim 10 and wherein:

each of the clamps has an interface with the pivot base.

14. The apparatus of claim 13 and wherein:

the interfaces between the clamps and pivot bases have interengaging detents providing interference between the clamp and respective pivot base when the clamp set screw is tightened, to prevent swiveling of the clamp on the pivot base.

15. The apparatus of claim 1 wherein:

the first U-shaped connector is a U-clamp having an upper arm and a lower arm; and said apparatus further comprises a swivel orientation lock between said transverse connector and said first connector, said lock including detents on the transverse connector and on said first connector.

16. The apparatus of claim 15 and wherein:

the detents include detent ridges and grooves on the transverse connector and detent ridges on the U-clamp.

17. The apparatus of claim 16 and wherein:

the transverse connector has a rod portion and a head portion at an end of the rod portion, the head portion having top and bottom surfaces and an aperture through them, and the detent ridges and grooves extend radially outward from the aperture on the top and bottom surfaces of the head portion.

18. The apparatus of claim 17 and wherein:

the one fastener is a set screw and has threads threaded into the lower arm of the U-clamp and has a bearing surface bearing downward on the upper arm of the U-clamp and holds at least one detent ridge of the U-clamp in at least one detent groove of the connector rod head to prevent swiveling of the rod about the aperture in the U-clamp.

19. In a system for spinal osteosynthesis including first and second generally parallel spinal rods implanted adjacent a spinal column, an apparatus for making a rigid connection between rods comprising:

first connector and a U-shaped second connectors connectable along the first and second spinal rods, respectively;

a transverse connector for location between the spinal rods;

a U-shaped third connector slidably connected to said transverse connector; and two fasteners, one of the fasteners connecting the first connector to the transverse connector when the first connector is connected to the first spinal rod, the other of the fasteners connecting the second connector to the third connector when said second connector is connected to the second spinal rod and said third connector is connected to said transverse connector, wherein said one of the fasteners is operable to lock said first connector to said transverse connector and said other of said fasteners is operable to lock said second and third connectors together while simultaneously locking said second connector to the second spinal rod and said third connector to said transverse connector for locking said transverse connector at different orientations with respect to the second rod.

* * * * *

UNITED STATES PATENT AND TRADEMARK OFFICE
CERTIFICATE OF CORRECTION

PATENT NO. : 5,716,355
DATED : February 10, 1998
INVENTOR(S) : Roger P. Jackson and Paul J. Wisnewski It is certified that error appears in the above-indentified patent and that said Letters Patent is hereby corrected as shown below:

On the title page, item [56]:

In "References Cited", add the following:
```
--5,047,029   9/1991    Aebi et al.
  5,261,909  11/1993    Sutterlin et al.
  5,397,363   3/1995    Gelbard
  5,403,316   4/1995    Ashman --.
```

Column 7, line 10, change "red" to --rod--.

Column 8, line 23, change "locating" to --locking--.

Column 10, line 24, after the word "connectors", add --each slidable--.

Signed and Sealed this

Eleventh Day of August 1998

*Attest:*

BRUCE LEHMAN

*Attesting Officer*   Commissioner of Patents and Trademarks